(12) United States Patent
Yoshida (10) Patent No.: US 7,736,510 B2
(45) Date of Patent: Jun. 15, 2010

(54) METHOD FOR PRODUCING METHANE GAS

(75) Inventor: Hiroyuki Yoshida, Sakai (JP)

(73) Assignee: Osaka Industrial Promotion Organization, Osaka (JP)

( * ) Notice: Subject to any disclaimer, the term of this patent is extended or adjusted under 35 U.S.C. 154(b) by 519 days.

(21) Appl. No.: 10/532,038

(22) PCT Filed: Oct. 20, 2003

(86) PCT No.: PCT/JP03/13397

§ 371 (c)(1),
(2), (4) Date: Dec. 20, 2005

(87) PCT Pub. No.: WO2004/037731

PCT Pub. Date: May 6, 2004

(65) Prior Publication Data

US 2006/0183951 A1   Aug. 17, 2006

(30) Foreign Application Priority Data

Oct. 22, 2002   (JP) .............................. 2002-306993

(51) Int. Cl.
*C02F 3/28*   (2006.01)
*C02F 11/04*   (2006.01)

(52) U.S. Cl. ........................................ 210/603; 210/613
(58) Field of Classification Search .................. 210/603, 210/761, 762, 612, 613
See application file for complete search history.

(56) References Cited

U.S. PATENT DOCUMENTS

| | | | | |
|---|---|---|---|---|
| 3,256,179 A | * | 6/1966 | Teletzke et al. | ............. 210/613 |
| 4,765,900 A | * | 8/1988 | Schwoyer et al. | ............ 210/603 |
| 5,057,220 A | * | 10/1991 | Harada et al. | ................ 210/605 |
| 6,143,176 A | * | 11/2000 | Nagamatsu et al. | ......... 210/603 |

FOREIGN PATENT DOCUMENTS

JP   55-88896   *   7/1980

(Continued)

OTHER PUBLICATIONS

Inoue, et al., "developing Wastewater Recycling Technologies by Catalytic Wet Oxidation Process", ZousuiGijutsu (1990) vol. 16, No. 3, p. 13-24 with translation.
Harada, et al., "Catalytic Wet Oxidation Process for Wastewater Treatment", Aromatics (1991) vol. 43, No. 11-12, p. 12-22 with translation.

*Primary Examiner*—Fred Prince
(74) *Attorney, Agent, or Firm*—Hamre, Schumann, Mueller & Larson, P.C.

(57) ABSTRACT

A practical technique that enables effective utilization of organic wastes is provided. In order to achieve the above-mentioned object, a method for producing methane gas from organic wastes according to the present invention includes: treating organic wastes with at least one of supercritical water and sub-critical water to convert the organic wastes into low molecular weight substances; and subjecting the low molecular weight substances to methane fermentation. According to the method, initially, the organic wastes are treated with at least one of the supercritical water and the sub-critical water so as to be converted into low molecular weight substances that are easily subjected to methane fermentation. Then, the treated substances are subjected to methane fermentation. Consequently, methane gas can be produced from the organic wastes at a high speed with high digestion efficiency.

13 Claims, 9 Drawing Sheets

FOREIGN PATENT DOCUMENTS

| | | |
|---|---|---|
| JP | 11-342379 | 12/1999 |
| JP | 2002-18393 | 1/2002 |
| JP | 2002-66507 | 3/2002 |
| JP | 2002-102828 | 4/2002 |
| JP | 2002-102897 | 4/2002 |
| JP | 2002-273493 | 9/2002 |

* cited by examiner

METHOD FOR PRODUCING METHANE GAS

TECHNICAL FIELD

The present invention relates to a method for producing methane gas from organic wastes.

BACKGROUND ART

Activated sludge (organic wastes) derived from the treatment of food wastes, sewage, and the like is generated in large quantities every day. For example, about 20 million tons of food wastes and about 90 million tons of sewage activated sludge are generated every year. Such organic wastes are incinerated and landfilled and are not utilized effectively in the present circumstances. Further, incineration requires a dehydration process, which is very expensive. Also, there is a problem of landfill sites for final wastes obtained after incineration, and such sites are expected to run out in several years. On this account, there is a need for a method for effectively reutilizing or recycling organic wastes.

As an attempt to reutilize organic wastes, it is proposed, for example, that fish offal and the like is treated with at least one of supercritical water and sub-critical water so as to be converted into low molecular weight substances such as acetic acid (see, for example, JP 11(1999)-342379 A and JP 2002-18393 A). However, in order to separate, collect, and reutilize acetic acid and the like obtained in this method, it is necessary to establish a further technique, which is yet to be in practical use.

On the other hand, subjecting sewage activated sludge to methane fermentation and recovering energy also has been attempted. A reaction path from a complex organic compound such as activated sludge to methane fermentation requires the following processes (1) to (4), for example.

(1) A complex organic compound is decomposed gradually into simple organic substances by hydrolysis.
(2) Simple organic acid is made into volatile organic acid by a fermentation action of acidogens.
(3) Long chain volatile organic acid with 3 or more carbon atoms is converted into acetic acid and $H_2$ by obligate hydrogen producing acetogens.
(4) The produced acetic acid and $H_2$ are converted into $CH_4$ by methanogens.

In such a conventional technique, it takes a very long time to decompose a complex organic compound such as sewage activated sludge by the action of bacteria. Further, methane fermentation generally requires two vessels, i.e., an acid production vessel and a methane fermentation vessel, in many cases. This is because unless sludge is decomposed finally into acetic acid, hydrogen, or carbon dioxide, the methanogens are not active and thus no methane is generated. In order to accelerate the decomposition of organic substances, a method including the following process is developed: a process in which sludge is pulverized into small pieces and mixed with dilution water so as to be solubilized, or a process in which an inhibitory substance in the decomposition is removed. Consequently, contact efficiency with bacteria is improved, and a reaction rate is increased. However, some organic substances cannot be decomposed into hydrogen and carbon dioxide, and the carbon digestion efficiency thereof is 20% to 50%. Thus, there is a need to treat undigested residual substances, which may require large waste water treatment equipment. Further, in the treatment of sewage sludge or dairy wastewater (cow dung, urine, and the like) using such a methane fermentation method, it is required to provide a retention time of 20 to 60 days in an actual plant and of 30 to 60 days in most cases. As described above, the conventional methane fermentation process is not practical since it is expensive and inefficient as a whole and may show a huge deficit even when electric power is sold.

DISCLOSURE OF INVENTION

Consequently, it is an object of the present invention to provide a practical technique that enables effective utilization of organic wastes.

In order to achieve the above-mentioned object, the present invention relates to a method for producing methane gas from organic wastes, including: treating organic wastes with at least one of supercritical water and sub-critical water to convert the organic wastes into low molecular weight substances; and subjecting the low molecular weight substances to methane fermentation.

In order to achieve the above-mentioned object, the present inventors made various studies. In the course of the studies, it was conceived that an organic waste was treated to be converted into low molecular weight substances and the treated substance was subjected to methane fermentation. Further studies in accordance with this conception led to the following findings. That is, by performing a treatment with supercritical water, sub-critical water, or both, conversion of an organic waste into low molecular weight substances, in which, for example, hydrolysis of a complex organic compound into simple organic compounds as well as long chain fatty acid and acid production as shown in the above-mentioned processes (1) to (3) are performed, can be carried out in 1 to 20 minutes, for example. Then, the present invention was arrived at by finding that the use of the low molecular weight treated substances allowed methane fermentation to be carried out in a short time of, for example, 5 to 24 hours, the carbon digestion efficiency thereof to be at least 90% or more, and preferably 97% or more, and the required treatment of a residual substance and waste water to be decreased. According to the present invention, it is possible to provide a method for producing methane that is, for example, economically efficient and environmentally friendly and achieves high-speed methane production with high digestion efficiency.

BEST MODE FOR CARRYING OUT THE INVENTION

Hereinafter, the present invention will be described in further detail.

In the present invention, a treatment with sub-critical water is more preferable than a treatment with supercritical water. Advantages of using sub-critical water are, for example, as follows: sub-critical water has a higher hydrolysis ability than that of supercritical water and thus various useful materials can be generated; sub-critical water has a lower decomposition capability than that of supercritical water and thus useful materials can be taken out without being decomposed into inorganic substances; a hydrolysis reaction is mostly an exothermic reaction and thus the use of exothermic heat enables a sufficient reduction in the running cost of a sub-critical water treatment; the condition of sub-critical water is milder than that of supercritical water and thus a safe treatment can be performed with an inexpensive treatment apparatus; and sub-critical water is water but has a high power of extracting oil and a fat and enables almost 100% extraction of such components from a raw material. Supercritical water of which temperature is not higher than about 700 K also can be used favorably in the present invention as long as the treatment is performed in the same manner as the sub-critical water treatment without mixing an oxidant or the like. This is because such a supercritical water treatment causes thermal decomposition almost without oxidization and a damaging effect on an apparatus is lower than that in supercritical oxidation known conventionally.

In the sub-critical water treatment, the treatment temperature is preferably in a range of, for example, 440 to 553 K, more preferably 470 to 553 K, and further preferably 493 to 553 K. The treatment pressure is, for example, 0.8 to 6.4 MPa, more preferably 1.5 to 6.4 MPa, and further preferably 2.3 to 6.4 MPa. The treatment time is, for example, 1 to 20 minutes, more preferably 1 to 10 minutes, and further preferably 1 to 5 minutes.

A treatment for converting an organic waste into low molecular weight substances can be performed in the following manner, for example. That is, in the case of a batch type treatment, an organic waste and water are fed to a pressure-and-heat-resistant reactor made of a material such as stainless steel, and the reactor is closed, for example. Then, the reactor is heated to a predetermined temperature, so that the inside of the reactor is under the high temperature and pressure condition. As a result, the water in the reactor is in a sub-critical state or a supercritical state, whereby the organic waste is converted into low molecular weight substances.

The treatment for conversion into low molecular weight substances includes, for example, a continuous type treatment in addition to the batch type treatment as mentioned above. In terms of practicability, a continuous type treatment is preferable.

The production method according to the present invention preferably includes, for example, separating a water phase from the treated substances, so that the water phase is subjected to methane fermentation. This allows methane fermentation to be carried out in a short time with high digestion efficiency. The water phase contains, for example, organic acid, phosphoric acid, amino acid, sugar, fatty acid, and the like. Among them, the water phase preferably contains organic acid. Organic acid includes, for example, lactic acid, acetic acid, pyroglutamic acid, formic acid, and the like. Among them, organic acid preferably includes acetic acid.

A method for separating and collecting a water phase from the treated substances is, for example, centrifugation. By centrifugation, the treated substances are separated into three layers formed of oil, water, and solids, respectively, due to its density difference, and the layer formed of a water phase is collected.

An organic waste to be applied to the production method according to the present invention is not particularly limited, and activated sludge derived from, for example, a substance obtained after a sewage treatment, a food waste, raw garbage, livestock excrement, and the like is applied.

Methane fermentation in the present invention is not particularly limited and can be carried out by applying a conventional method as appropriate. For example, the low molecular weight treated substances and methane fermenting microorganisms are fed into a methane fermentation vessel, the methane fermentation vessel is kept at a predetermined temperature, and fermentation is carried out for a predetermined retention time while the contents of the methane fermentation vessel are stirred as appropriate. Then, the generated methane gas is collected.

Figure 1:
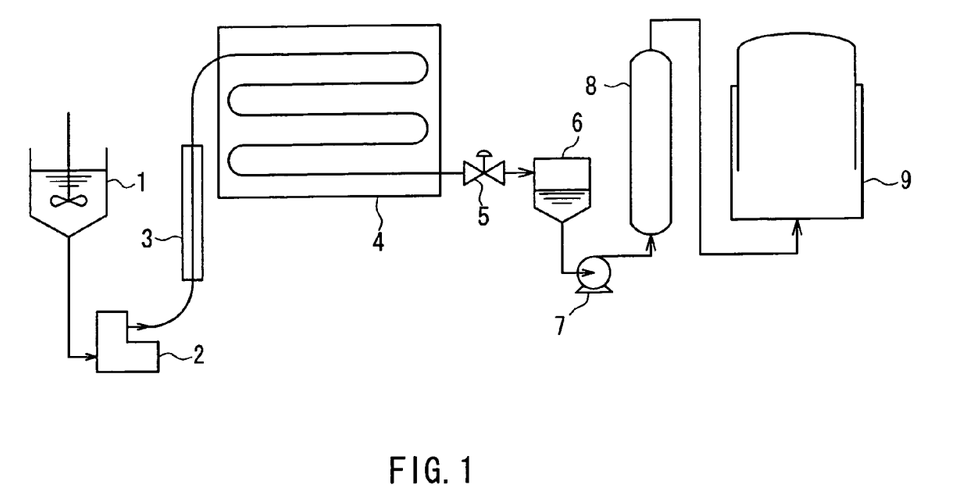
FIG. 1 is a schematic view showing an example of a method for producing methane gas according to the present invention.

Next, an example of the configuration of an apparatus for producing methane gas for use in the method for producing methane gas according to the present invention is shown in FIG. 1. As shown in the figure, the apparatus is constituted by two units, i.e., a sub-critical water treatment unit and a methane fermentation unit. The sub-critical water treatment unit includes a feed tank 1, a heater 3, and a sub-critical reaction device 4 as principal components. These components are connected via pipes in this order. The feed tank 1 is provided with a stirrer, and a high pressure pump 2 is arranged in a pipe connecting the feed tank 1 and the heater 3. The methane gas fermentation unit includes an intermediate tank 6, a metering pump 7, a fermentation vessel 8, and a gas holder 9 as principal components. Theses components are connected via pipes in this order. The intermediate tank 6 is connected with a pipe led from the sub-critical reaction device of the sub-critical unit, and a back pressure valve 5 is arranged in this pipe.

This apparatus produces methane gas in the following manner, for example. Initially, an organic waste is put into the feed tank 1. The organic waste may be stirred with the stirrer. The organic waste is introduced to the heater by the high pressure pump 2 so as to be heated to a predetermined temperature. The heated organic waste is introduced to the sub-critical reaction device 4 as it is, where the organic waste is subjected to a sub-critical water treatment to be converted into low molecular weight substances. The low molecular weight substances are sent to the intermediate tank 6 to be stored therein temporarily. Then, via the metering pump 7, a certain amount of low molecular weight substances in the intermediate tank 6 is sent to the fermentation vessel 8 to be subjected to a methane fermentation treatment with bacteria therein. Methane gas generated in the fermentation vessel 8 is sent through the pipe to the gas holder 9, where the methane gas is collected.

Methane fermentation of the low molecular weight substances may be either batch type fermentation or continuous type fermentation. A description will be given of continuous type methane fermentation with reference to FIG. 2. The figure is a view showing an example of the configuration of a device for continuous type methane fermentation. As shown in the figure, the device includes an intermediate tank 6 for storing the low molecular weight substances, a metering pump 7, a fermentation vessel 8, and a gas holder 9 as principal components. These components are connected via pipes in this order. The intermediate tank 6 is provided with a stirrer. The fermentation vessel 8 is arranged in a thermostat 10 containing a liquid such as water therein. Both the fermentation vessel 8 and the thermostat 10 are provided with a stirrer. A pipe is led from an upper part of the thermostat 10, and an end of the pipe is led to a lower part of the thermostat 10. A circulating pump 15 and a heater 16 are arranged in this pipe. A temperature controller 17 is arranged at another lower part of the thermostat 10. The temperature controller 17 controls the heater 16 while monitoring the temperature in the thermostat 10. A pipe 12 is led from a ceiling part of the fermentation vessel 8, and an end of the pipe is led to the gas holder 9. A gas sampling valve 14 is arranged in the pipe 12. Further, a pipe 11 is led from an upper side face of the fermentation vessel 8, and an end of the pipe 11 is led to a liquid waste tank 13.

Figure 2:
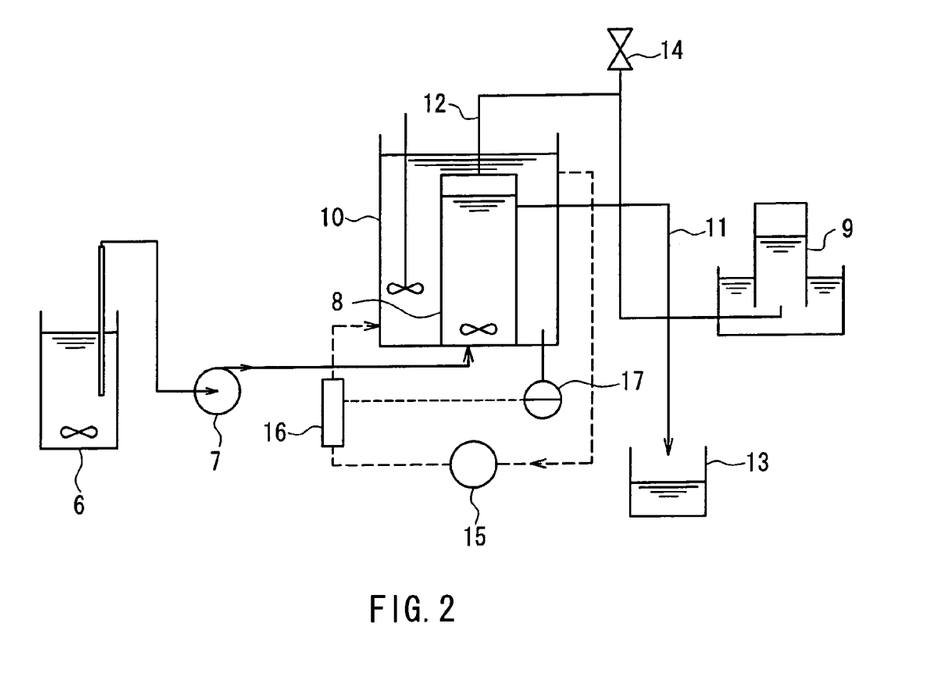
FIG. 2 is a schematic view showing an example of a device that can be used for methane fermentation according to the present invention.

Continuous type methane fermentation by this device is carried out in the following manner, for example. Initially, the low molecular weight substances in the intermediate tank 6 are metered to the fermentation vessel 8 by the metering pump 7. On the other hand, the liquid in the thermostat 10 is stirred with the stirrer and circulated by the circulating pump 15. The temperature controller 17 monitors the temperature in the thermostat 10 and controls the heater 16 based on this information, so that the liquid in the thermostat 10 is kept at a certain temperature (for example, 37° C. to 55° C.). In the fermentation vessel 8, methane fermentation is carried out by bacteria while the contents are stirred with the stirrer. Generated gas is sent through the pipe 12 to the gas holder 9, where the gas is collected. In order to monitor the state of fermentation, gas is sampled as appropriate from the gas sampling valve 14. When the low molecular weight substances in the fermentation vessel 8 are decreased, the low molecular weight substances are added by the metering pump 7. When the low molecular weight substances are added in an amount exceeding a certain level, the excess amount of low molecular weight substances are sent to the liquid waste tank 13 through the pipe 11. In this manner, methane fermentation can be carried out continuously.

As microorganisms for use in the methane fermentation, conventionally known methanogens or the like can be used as appropriate. When the organic waste to be used is, for example, sewage activated sludge, digested sludge from a sewage treatment plant can be used as a microorganism group for use in the methane fermentation. The microorganism group for use in the methane fermentation is preferably rich in methanogens and may include acid producing bacteria. Further, the microorganism group for use in the methane fermentation preferably is acclimated to acetic acid before use. This increases the efficiency of the methane fermentation. The number of acclimation days is not particularly limited and may be 15 to 30 days, for example.

The temperature in the methane fermentation vessel can be set at a conventionally known temperature suitable for microorganisms for use in methane fermentation, and may be 37° C. to 55° C., for example. The retention time of the low molecular weight treated substances in the methane fermentation vessel is in a range of, for example, 5 to 48 hours, preferably 5 to 24 hours, and more preferably 5 to 12 hours. As described above, in the methane fermentation according to the present invention that achieves high speed and high digestion efficiency, a reaction rate in the fermentation vessel is about 15 to 150 times faster than that in conventional fermentation. Accordingly, the volume of the fermentation vessel can be reduced to $1/15$ to $1/150$, and energy for keeping the fermentation vessel at a constant temperature also can be reduced to $1/15$ to $1/150$ of energy required conventionally.

In order to carry out the methane fermentation more efficiently, a buffer, a supplementary nutrient, and the like can be added further to the methane fermentation vessel as appropriate. The buffer, the supplementary nutrient, and the like are not particularly limited, and conventionally known ones can be used.

In the present invention, the carbon digestion efficiency in the methane fermentation is, for example, 80% or more, preferably 90% or more, and more preferably 97% or more. The carbon digestion efficiency can be calculated by using total organic carbon (TOC). For example, the carbon digestion efficiency can be obtained based on the following formula by performing component analysis of an original solution to be subjected to methane fermentation and a liquid waste obtained after the methane fermentation. The TOC can be measured with, for example, a TOC analyzer. The TOC analyzer is a device for obtaining TOC from a difference between total carbon (TC) and inorganic carbon (IC).

Carbon digestion efficiency=(original solution TOC−liquid waste TOC)/original solution TOC×100

Methane gas generated by the methane fermentation and collected can be used in many fields. For example, the methane gas can be converted into heat by a gas-fired boiler, converted into gas-generated power, used as a supply source of hydrogen for fuel cells, and the like.

In the present invention, activated sludge is treated with at least one of supercritical water and sub-critical water so as to be converted into low molecular weight substances, whereby a useful material can be produced.

The treatment for converting activated sludge into low molecular weight substances can be performed in the same manner as the treatment for converting an organic waste into low molecular weight substances as described with regard to the method for producing methane gas. The process of the treatment for conversion into low molecular weight substances results in low molecular weight treated substances containing phosphoric acid, organic acid, fatty acid, amino acid, sugar, and the like. It is preferable that useful materials are separated from these components and purified. The organic acid includes, for example, lactic acid, formic acid, acetic acid, pyroglutamic acid, propionic acid, and the like. The fatty acid includes, for example, palmitoleic acid, palmitic acid, oleic acid, stearic acid, and the like. The amino acid includes, for example, alanine, aspartic acid, glycine, isoleucine, leucine, phenylalanine, and the like. The sugar includes, for example, glucose, fructose, and the like. Among them, phosphoric acid, for example, is taken out from a phosphate ore as a limited resource presently. However, the present invention is to be expected as a new technique for taking out phosphoric acid. Further, lactic acid, for example, is useful as a material of biodegradable plastic. The generation amount of such useful materials contained in the low molecular weight treated substances varies depending upon the treatment conditions in the process of the treatment for conversion into low molecular weight substances such as, for example, a treatment temperature, a treatment pressure, and a treatment time. Thus, by adjusting the treatment condition, it is possible to produce a useful material selectively.

Hereinafter, an example of the present invention will be described. However, the present invention is not limited to this example.

EXAMPLE

As described below, a batch-type sub-critical water treatment was performed using activated sludge as an organic waste. Then, low molecular weight treated substances obtained by the sub-critical water treatment were subjected to methane fermentation, and methane gas was collected. At the same time, an oil phase, a water phase, and a solid phase are separated, collected, and subjected to component analysis.

(Organic Waste)

As an organic waste, surplus activated sludge provided by Senboku Sewage Treatment Plant of the Sewage and Wastewater Management Department of the Construction Bureau in Sakai city in Osaka was used. In order to reduce the water content of this activated sludge, it was allowed to settle naturally all day and night and then filtered. The water content was 99.6% before the precipitation, 99.0% after the precipitation, and 97.5% after the filtration. The water content of the sludge was obtained from a change in weight before and after the sludge was stirred sufficiently and dried at 80° C. for 2 days.

(Reactor)

Figure 3:
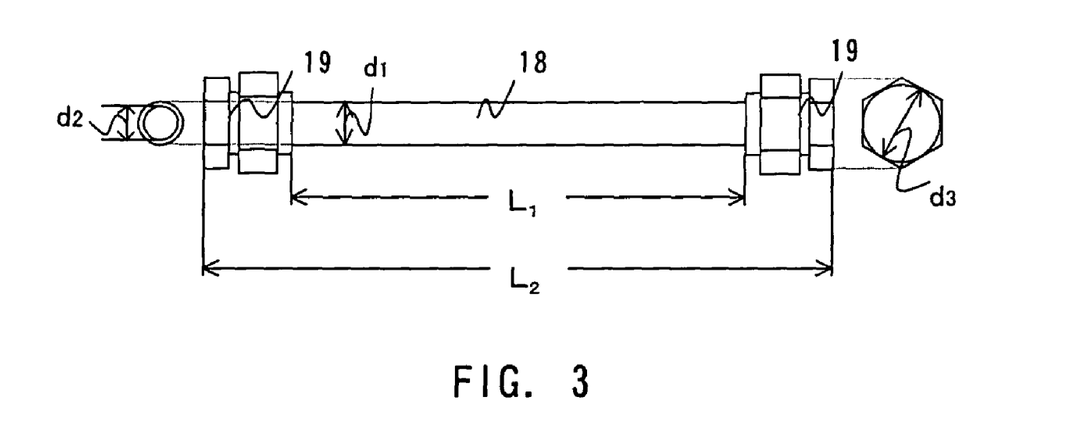
FIG. 3 is a schematic view showing a reactor used in an example.

An outline of a reactor used in the sub-critical water treatment is shown in FIG. 3. The reactor has a configuration in which caps 19 are attached to both ends of a pipe 18. In FIG. 3, reference numeral $d_1$ denotes an outer diameter of the pipe 18, $d_2$ denotes an inner diameter of the pipe 18, and $d_3$ denotes a diameter of an inscribed circle of the cap 19. A length $L_1$ represents the shortest distance between the caps 19, and a length $L_2$ represents the entire length of the reactor.

The reactor was manufactured by using the pipe 18 made of stainless steel (material: SUS316) having an outer diameter $d_1$ of 9.5 mm and an inner diameter $d_2$ of 7.5 mm. The pipe 18 was cut into a length of about 15.5 cm with a pipe cutter, and adjusted to have a length of about 15.0 cm by using a lathe. In order to prevent leakage of contents of the reactor during the sub-critical water treatment and increase the sealing property, cut areas of the pipe 18 were ground to be smooth, and an outer side and an inner side of each of the cut areas ware rounded. After that, the cut-out pipe 18 was washed, and the caps 19 (manufactured by Swagelok Company; trade name: SS-600-C) were attached to the respective ends of the pipe 18. Each of the caps 19 was attached by being screwed onto the pipe 18 by hand and then turned one and a quarter turns with a monkey wrench. When the caps 19 were fixed to the pipe 18 in this manner, the manufactured reactor had an entire length $L_2$ of 16.5 cm and a shortest distance $L_1$ between the caps 19 of 12.0 cm. The inner volume of the reactor was calculated in the following manner. That is, water of 298 K that was allowed to stand for 1 day in an air thermostat (manufactured by Sanyo Electric Co., Ltd.; trade name: INCUBATOR MIR-251) set at 298 K was put into the reactor, the mass of the water was measured, and the inner volume was calculated by using the density ($\rho$=996.95 kg/m$^3$) of the water. The inner volume of the reactor was 7.0 cm$^3$.

(Salt Bath)

As a thermostat for keeping the reactor during the sub-critical water treatment at a high constant temperature, a salt bath (manufactured by Thomas Kagaku Co., Ltd.) was used. As a heat medium in the salt bath, a blended salt (melting point: 413 K) in which potassium nitrate and sodium nitrite were mixed at a ratio of 1:1 was used. The amount of salt used was 0.018 m$^3$. The salt bath had a temperature in a range of 453 K to 773 K and temperature stability of ±0.5 K. The adjustment of the temperature was carried out by a PID-control-system digital temperature indicating controller.

(Deoxidation in the Reactor)

Before the reactor was loaded with a sample to be subjected to the sub-critical water treatment, the inside of the reactor was replaced with Ar previously. After that, the reactor was loaded with the activated sludge sample (0.8 g of sludge, 4.0 g of ultrapure water) prepared as described above. Before the reactor was sealed, Ar was allowed to flow again for about 30 seconds, thereby performing deoxidation. Thereafter, the reactor was sealed.

(Sub-Critical Water Treatment)

Figure 4:
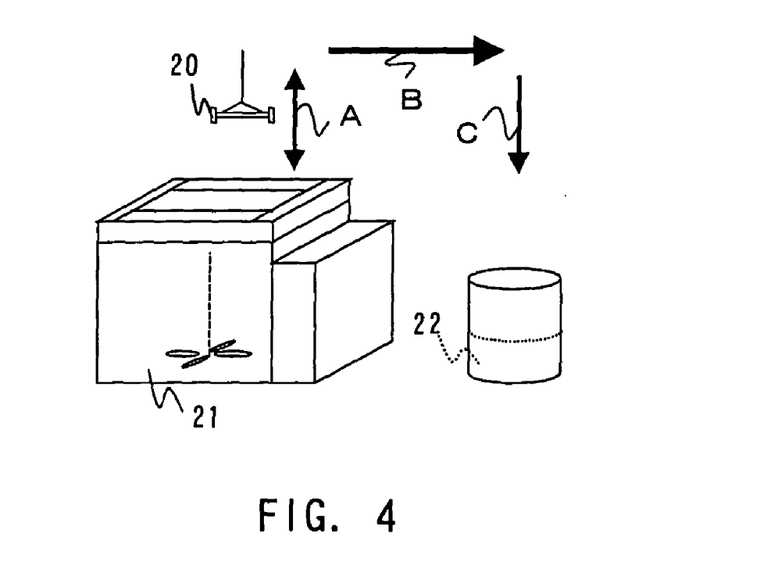
FIG. 4 is a view for explaining an example of processes of a sub-critical water treatment.

An outline of the sub-critical water treatment is shown in FIG. 4. A reactor 20 that was loaded with the sample and sealed as described above was moved in a downward direction of an arrow A to be put into a salt bath 21 that was stabilized at a predetermined temperature (440 to 553 K). After a predetermined period of time (for example, 1 to 20 minutes), the reactor 20 was moved in an upward direction of the arrow A to be taken out of the salt bath 21 immediately, and then moved in directions of arrows B and C immediately to be put into a large amount of quenching water 22, where the reactor 20 was quenched rapidly. In this sub-critical water treatment, the temperature of the salt bath 21 was regarded as a reaction temperature, and the time for which the reactor 20 was in the salt bath 21 was regarded as a reaction time.

(Separation and Collection of an Oil Phase, an Oil and Fat Phase, a Water Phase, and a Solid Phase)

After the activated sludge was subjected to the sub-critical water treatment as described above, contents of the reactor were taken out to a test tube D having an inner volume of 8.0 cm$^3$. The test tube D was loaded in a centrifugal separator (manufactured by Kubota Corporation; trade name: KN-70), and centrifugation was performed at a rotation speed of 2500 rpm for 10 minutes. As a result, the contents of the test tube D formed multiple layers due to their mass difference. The uppermost layer was formed of liquid oil, below which a layer of solid oil and fat and a layer of water were formed in this order, and the lowermost layer was formed of solids. Components of the respective layers, which were referred to as an oil phase, an oil and fat phase, a water phase, and a solid phase, were separated and collected in the following manner.

Initially, about 1.0 cm$^3$ of hexane was added to the test tube D, so that the oil phase was dissolved. By taking out the hexane phase, the oil phase was separated and collected. The hexane phase was taken out with a Pasteur pipette and moved to a test tube E. By repeating this operation twice or three times, the oil phase in the test tube D was separated and collected in the test tube E in a state where the oil phase was dissolved in the hexane.

Next, the oil and fat phase and a part of the water phase in the test tube D were taken out to a test tube F. In order to collect the water phase that was moved with the oil and fat phase from the test tube F, about 5.0 cm$^3$ of ultrapure water was added to the test tube F, and centrifugation was performed at 2500 rpm for 10 minutes. After that, the water phase present below the oil and fat phase was taken out with a Pasteur pipette and moved to a measuring flask G having an inner volume of 250 cm$^3$. By repeating this operation twice or three times, a part of the water phase was collected in the measuring flask G. Further, in the test tube F, the oil and fat phase was separated and collected from the test tube D.

Then, the remaining water phase was taken out from the test tube D from which the oil phase and the oil and fat phase were removed, with a Pasteur pipette and collected in the measuring flask G. In order to collect the water phase and a water-soluble component in the solid phase remaining in the test tube D, about 5.0 cm³ of ultrapure water was added to the test tube D, and centrifugation was performed at 2500 rpm for 10 minutes. After that, the water phase on top of the solid phase was moved to the measuring flask G with a Pasteur pipette. By repeating this operation twice or three times, the water phase was separated and collected in the measuring flask G from the test tube D. As a result, the solid phase was separated and collected in the test tube D.

The water phase separated and collected as described above contains a suspended oil and fat substance that was not separated by the centrifugation. Thus, the oil and fat substance present in the water phase was removed by filtration. Ultrapure water was added to the water phase separated and collected in the measuring flask G up to a scale of 250 cm³, and the obtained solution was allowed to pass through a membrane filter having a pore diameter of about 0.22 µm. The membrane filter was washed with about 250 cm³ of ultrapure water after the filtration so that a water phase component was removed from the membrane filter, and then dried at a room temperature of 25° C. for 3 days. The oil and fat substance thus collected was treated as an oil and fat phase.

As described above, the contents of the reactor after the sub-critical water treatment were separated into four phases, i.e., the oil phase, the oil and fat phase, the water phase, and the solid phase, and collected separately. Each of the solid phase and the oil and fat phase was air-dried and then had its mass measured. Further, the oil phase dissolved in the hexane was air-dried so as to evaporate the hexane, and had its mass measured.

Figure 5:
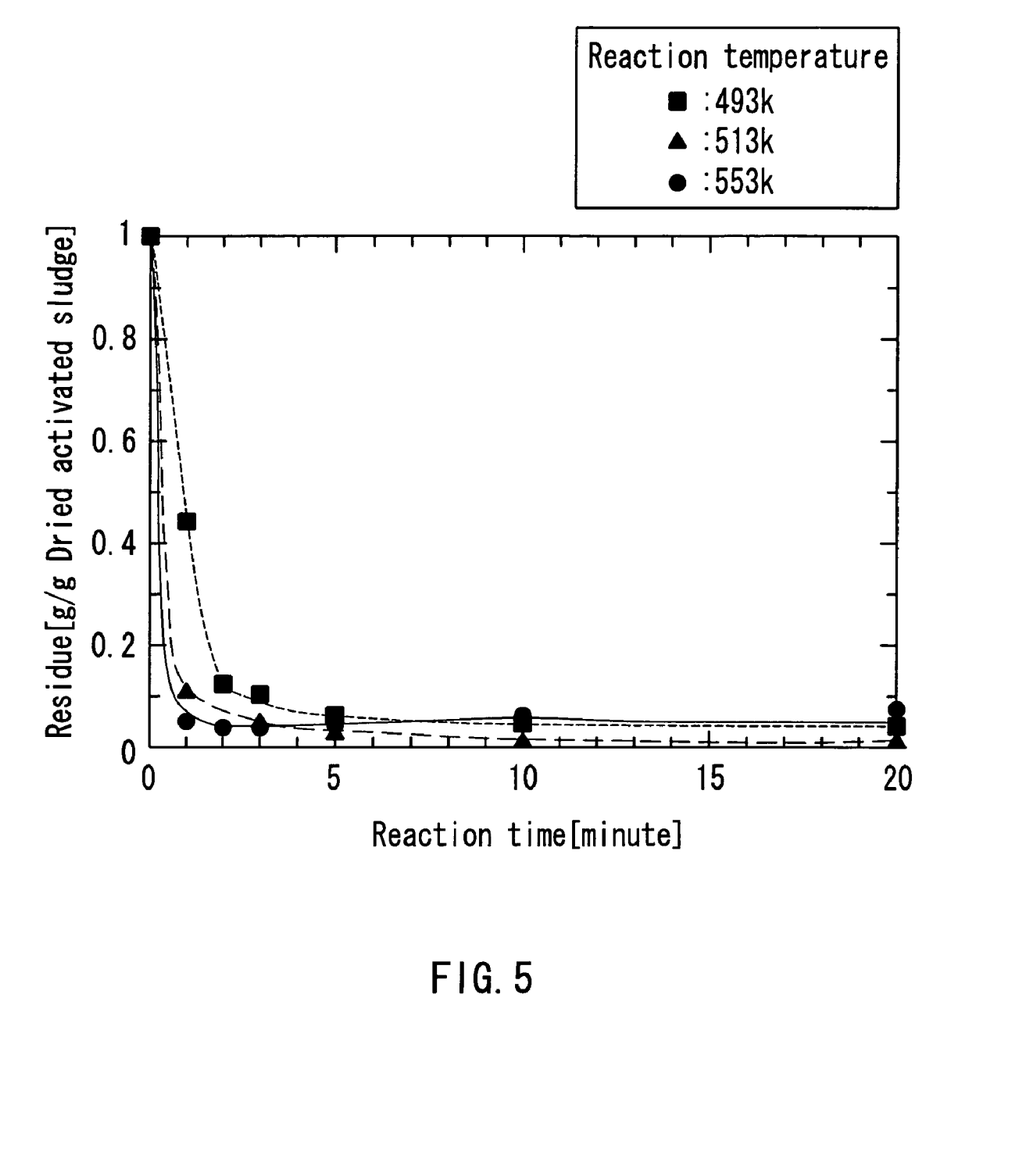
FIG. 5 is a graph showing an example of time course of residue of a solid at respective reaction temperatures.

The activated sludge before the sub-critical water treatment was a black slurry material. However, by performing the sub-critical water treatment, the black solid was reduced, and a liquid phase became dark brown. FIG. 5 shows time course of the residue of the solid phase at reaction temperatures of 493 K, 513 K, and 553 K, respectively. In the present example, the yield was obtained based on the following Formula (1). As shown in FIG. 5, a higher reaction temperature allowed the residue of the solid phase to be constant earlier. Accordingly, it was shown that a higher reaction temperature allowed the sample to be converted into low molecular weight substances in a shorter time by the sub-critical water treatment.

$$\text{Residue or yield (g/g dried activated sludge)}=\text{objective material mass (g)/dry mass of activated sludge (g)} \quad (1)$$

Figure 6:
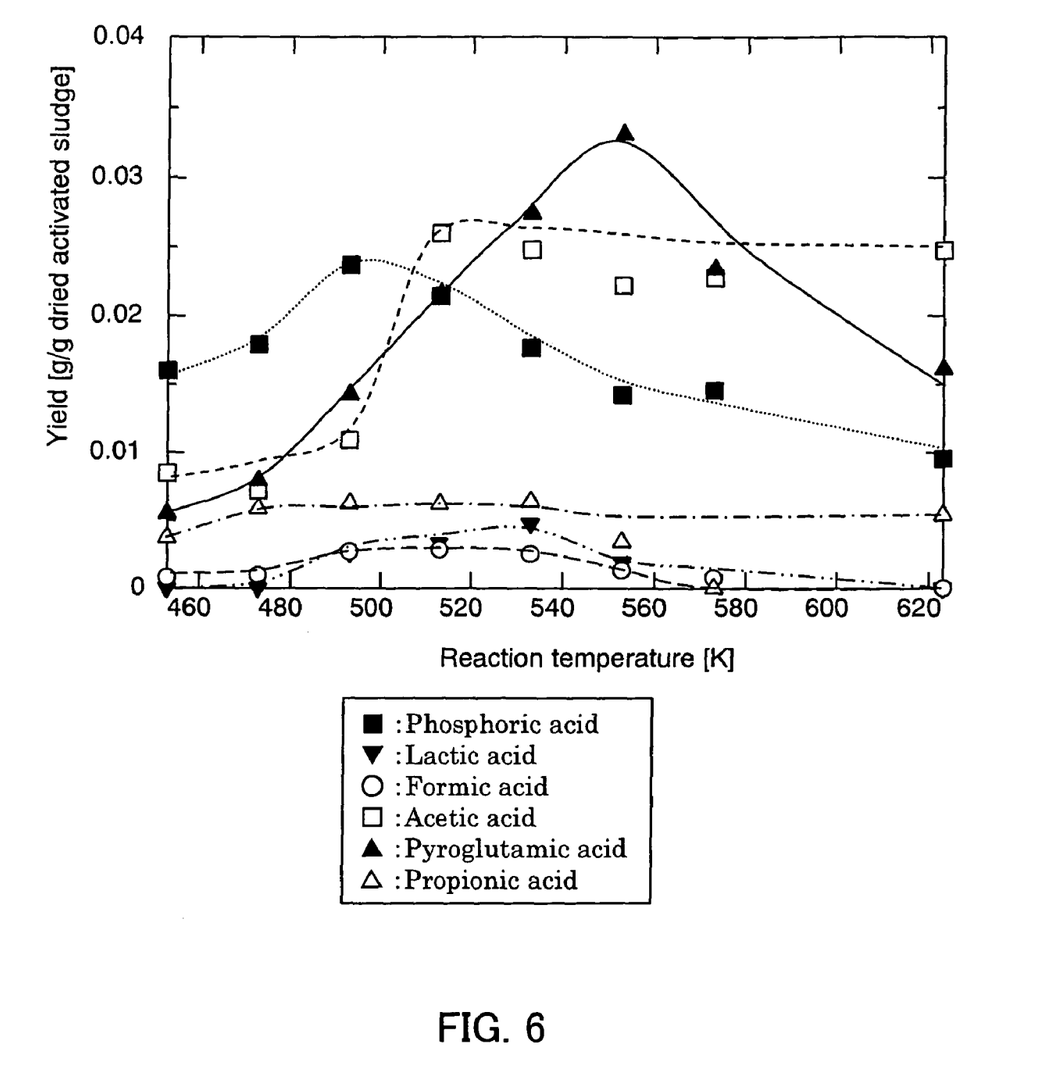
FIG. 6 is a graph showing an example of effect of reaction temperature on the yield of phosphoric acid and organic acid in a water phase.

Organic acid and phosphoric acid in the water phase separated and collected as described above were analyzed and measured by using a high-performance liquid chromatography (HPLC) organic acid analysis system (manufactured by Shimadzu Corporation; trade name: LC-10A; separation method: ion-exclusion chromatography; detection method: post column pH buffering conductometric detection method). FIG. 6 shows the effect of a reaction temperature on the yield of organic acid and phosphoric acid in the case where the reaction time of the sub-critical water treatment was made constant (10 minutes). The yield was calculated based on the above-mentioned Formula (1). As shown in FIG. 6, phosphoric acid, acetic acid, and pyroglutamic acid were the three major acids present in the water phase, and other organic acids were low in yield. The yield of the phosphoric acid varied depending upon the reaction temperature, which was 0.024 as a maximum value at 493 K and decreased thereafter.

The yield of the acetic acid was 0.026 at 513 K and became constant thereafter. The yield of the pyroglutamic acid was 0.033 at 553 K and decreased thereafter. The yields of other organic acids were almost constant regardless of the reaction temperature. Since there are useful components that have different peaks depending upon the reaction temperature, it is possible to take out the respective components selectively. In the method for producing methane gas according to the present invention, the yield of acetic acid was important, and thus a temperature of 513 K was most suitable in the present example.

Figure 7:
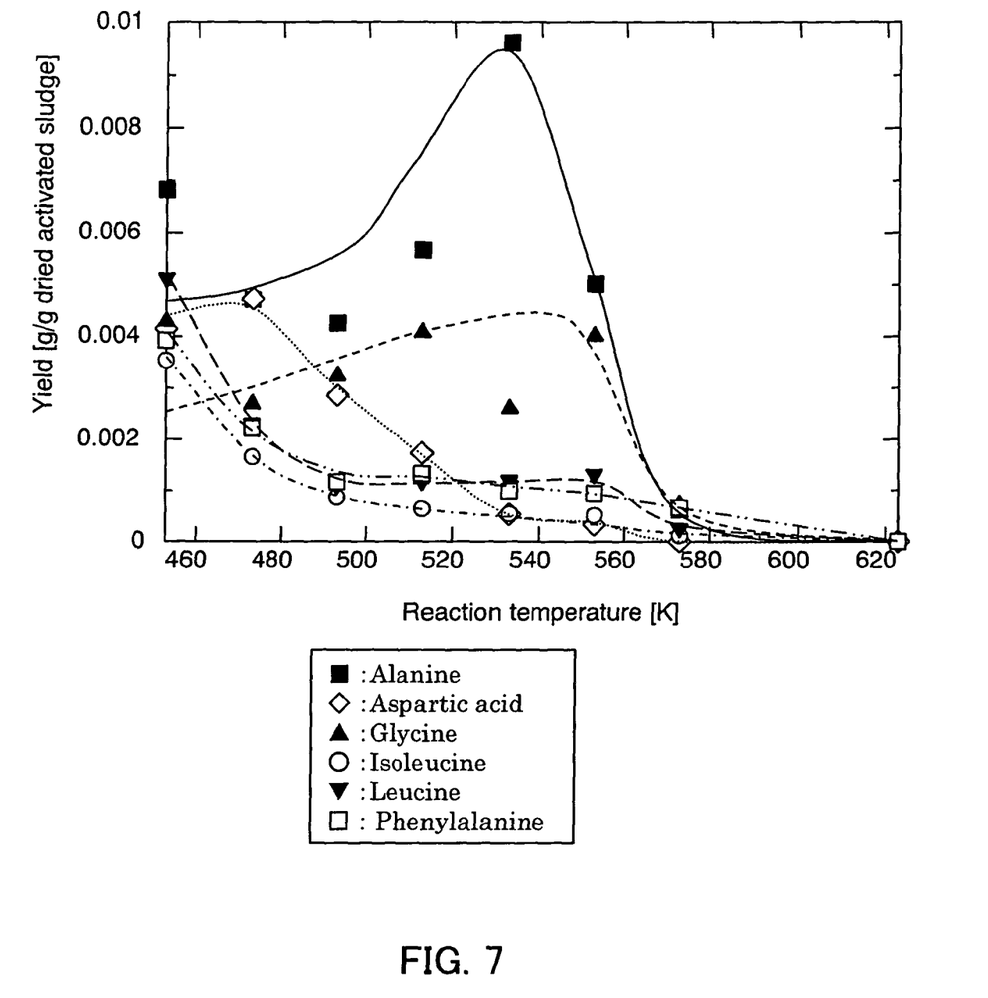
FIG. 7 is a graph showing an example of effect of reaction temperature on the yield of amino acid in the water phase.

Next, amino acid in the water phase was analyzed and measured by using a high-performance liquid chromatography (HPLC; manufactured by Shimadzu Corporation; trade name: LC-10A; post column derivatization method; detector: PF-10A$_{XL}$ fluorescent detector). FIG. 7 shows the effect of reaction temperature on the yield of amino acid in the water phase in the case where the reaction time of the sub-critical water treatment was made constant (10 minutes). The yield was calculated based on the above-mentioned Formula (1). As shown in FIG. 7, although the water phase contained various kinds of amino acids, the major amino acids present therein were glycine and alanine. The yield of the alanine was 0.009 as a maximum value at 533 K. The yield of the glycine was 0.004 as a maximum value at 553 K and decreased thereafter.

Figure 8:
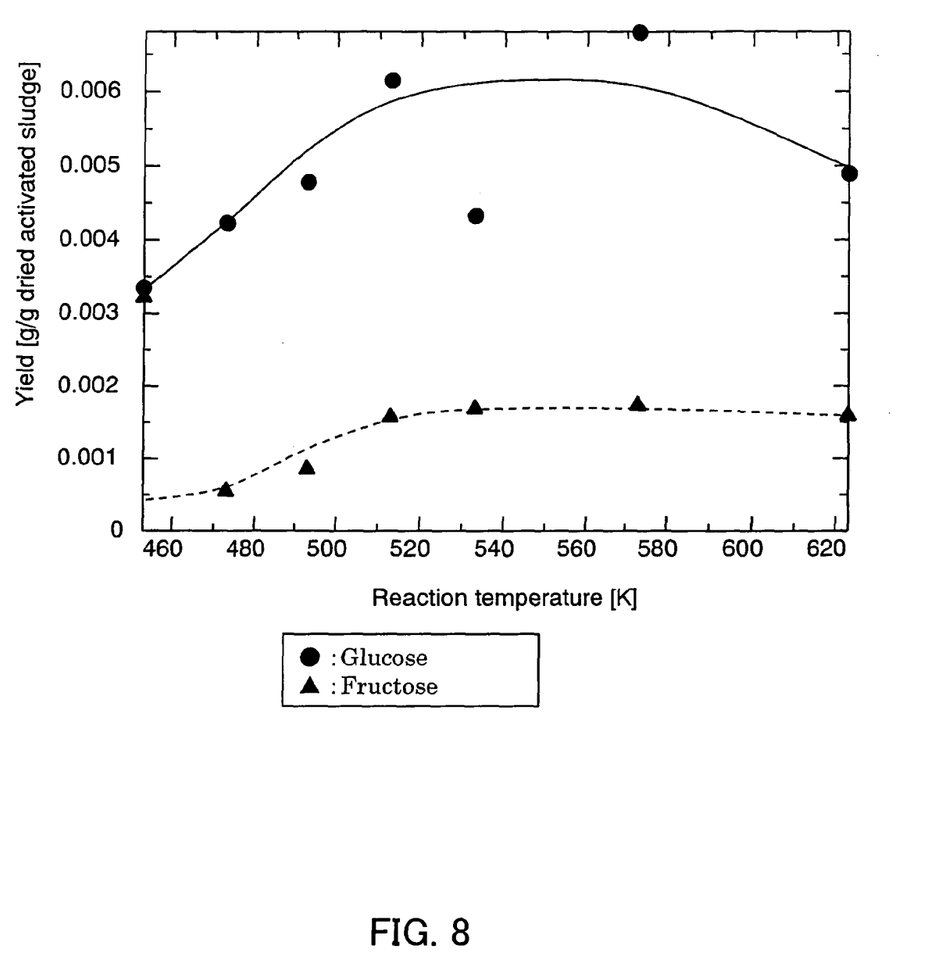
FIG. 8 is a graph showing an example of effect of reaction temperature on the yield of sugar in the water phase.

Further, sugar in the water phase was analyzed and measured by using a high-performance liquid chromatograph (HPLC) sugar analysis system (manufactured by JASCO Corporation; HSS-1500; differential refractometer: polarization type). FIG. 8 shows the effect of reaction temperature on the yield of sugar in the water phase in the case where the reaction time of the sub-critical water treatment was made constant (10 minutes). The yield was calculated based on the above-mentioned Formula (1). As shown in FIG. 8, glucose and fructose as monosaccharide were the major sugars present in the water phase. Both the sugars had their yields increased at around 513 K, and the yield of the glucose was decreased after its peak, while the yield of the fructose became constant thereafter.

Figure 9:
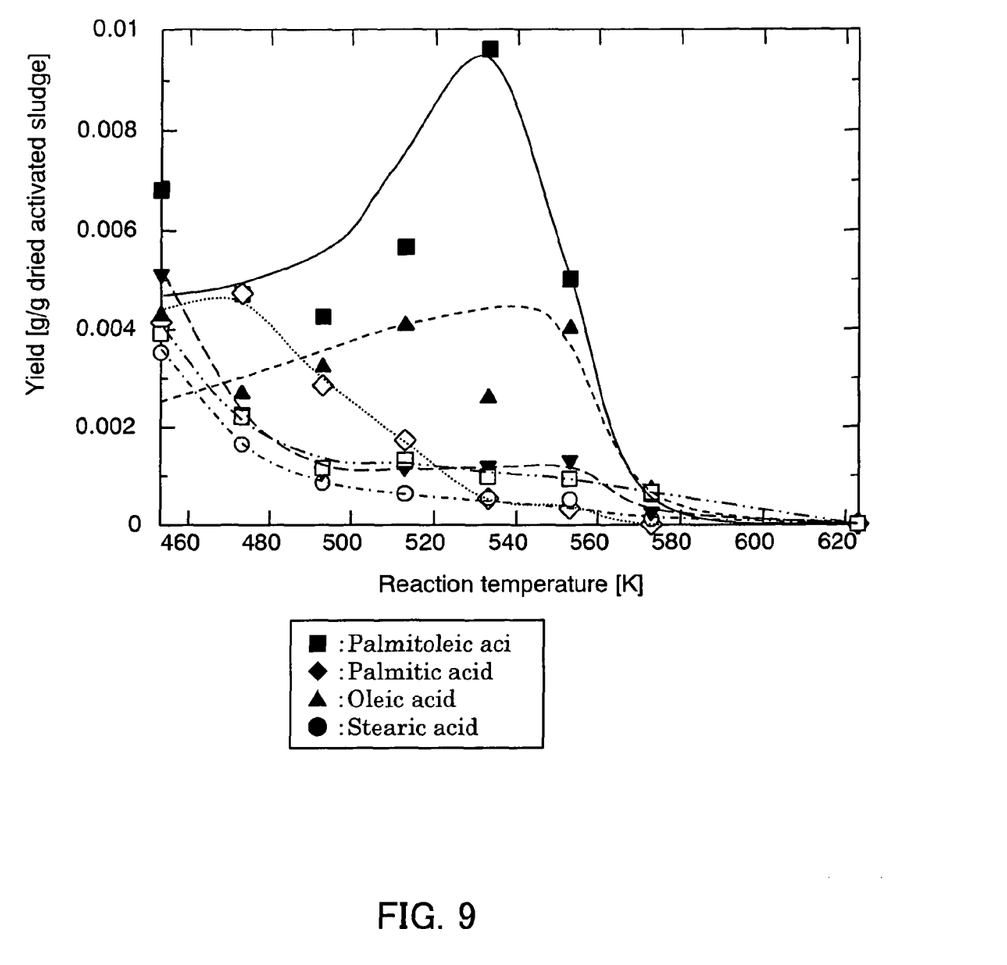
FIG. 9 is a graph showing an example of effect of reaction temperature on the yield of fatty acid in an oil phase.

Further, fatty acid in the oil phase separated and collected as described above was analyzed. Components in the oil phase were converted into trimethylsilyl derivatives, and the obtained derivatives were analyzed and measured with a gas chromatograph mass spectrograph (manufactured by Shimadzu Corporation; trade name: GCMS-QP5050). FIG. 9 shows the effect of reaction temperature on the yield of the components in the oil phase in the case where the reaction time of the sub-critical water treatment was made constant (10 minutes). The yield was calculated based on the above-mentioned Formula (1). As shown in FIG. 9, palmitoleic acid, palmitic acid, oleic acid, and stearic acid were the major components present in the oil phase. The yields of the respective components were increased as the reaction temperature became higher. Above all, the yield of the oleic acid was the highest, which was 0.015 at 623 K.

(Methane Fermentation)

Methane fermentation was carried out using the low molecular weight organic substances obtained by the sub-critical water treatment as described above.

Figure 10:
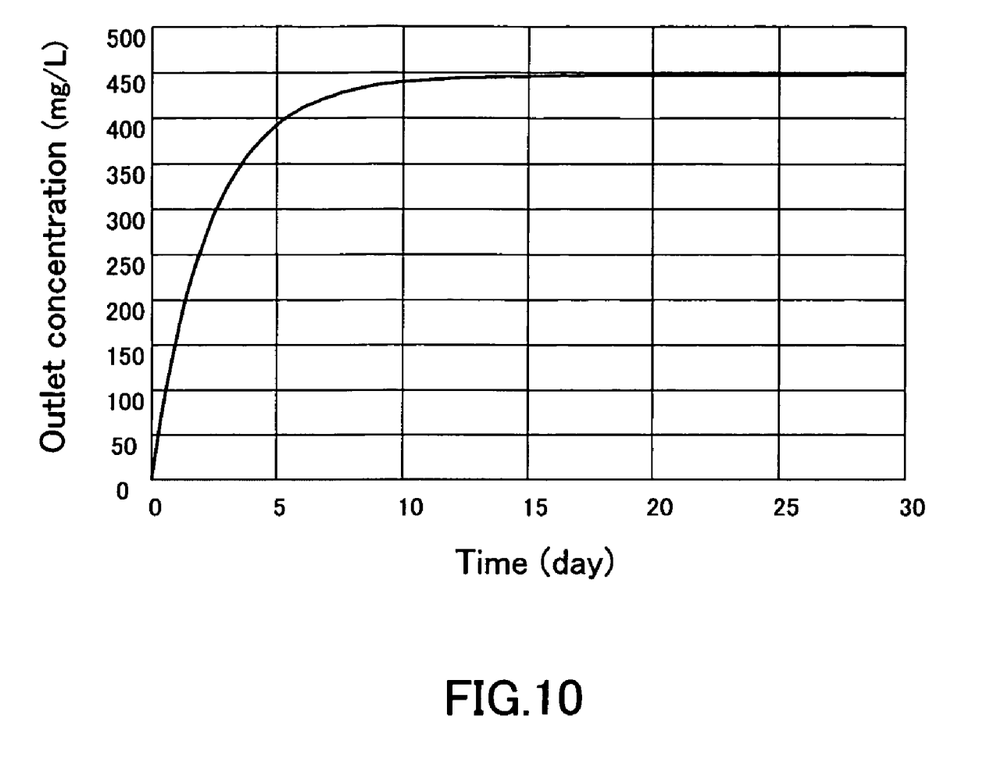
FIG. 10 is a graph showing an example of time course of methane gas concentration produced in acclimation process of activated sludge using acetic acid.

Initially, sludge from a sewage treatment-digestion vessel to be used as a microorganism group in methane fermentation was adjusted to a VSS (loss on ignition of a suspended solid (SS)) of 1000 mg/l, put into a well-closed container of 10000 ml provided with a stirrer, and kept at a constant temperature in a thermostat of 35° C. Then, an aqueous solution adjusted to have 5000 mg/l of acetic acid was injected thereto continuously at a load of 400 ml per day, and the activated sludge containing methanogens was subjected to acclimation to acetic acid for 30 days. FIG. 10 shows time course of methane gas concentration produced in acclimation process of the sludge using acetic acid. As shown in FIG. 10, the microorganism group for use in methane fermentation was generated in about 15 days. The activated sludge subjected to the acclimation was adjusted to a VSS of 4000 mg/l, put into a well-closed fermentation container of 2000 ml in which the contents thereof were allowed to be stirred with a stirrer, and used in methane fermentation in a thermostat of 35° C.

Next, a water phase obtained by decomposing the sewage sludge by sub-critical water further was subjected to separation and concentration with an ion-exchange resin, so that an aqueous solution having a composition as shown in the following Table 1 was prepared as an original solution for the methane fermentation.

TABLE 1

| Composition | Weight rate (mass %) | Concentration (mg/l) |
|---|---|---|
| Acetic acid | 25 | 500 |
| Short chain fatty acid | 58 | 1160 |
| Formic acid | 17 | 340 |
| Total | 100 | 2000 |

Figure 11:
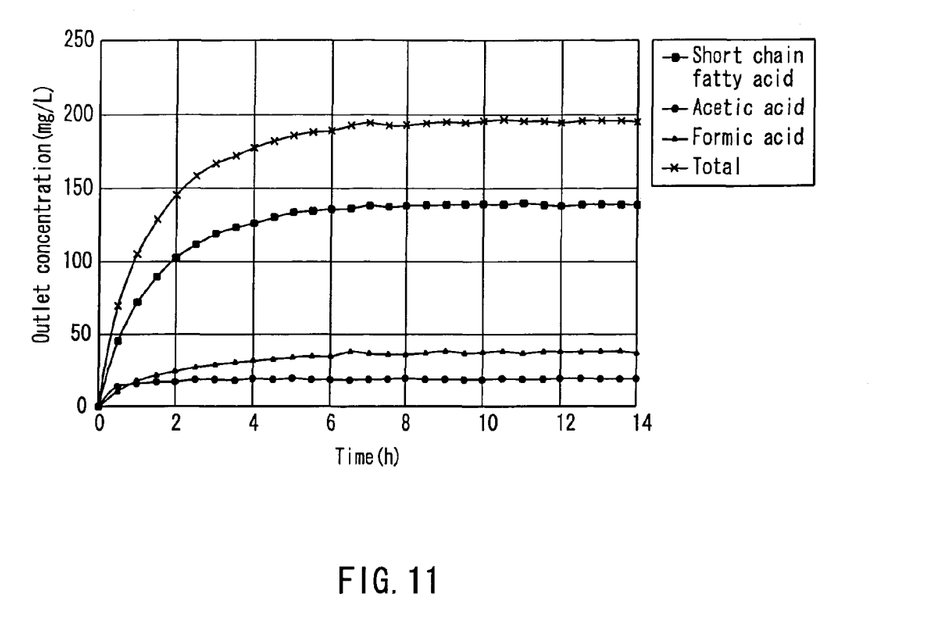
FIG. 11 is a graph showing an example of a time course of composition of a discharged aqueous solution in continuous methane fermentation.
Figure 12:
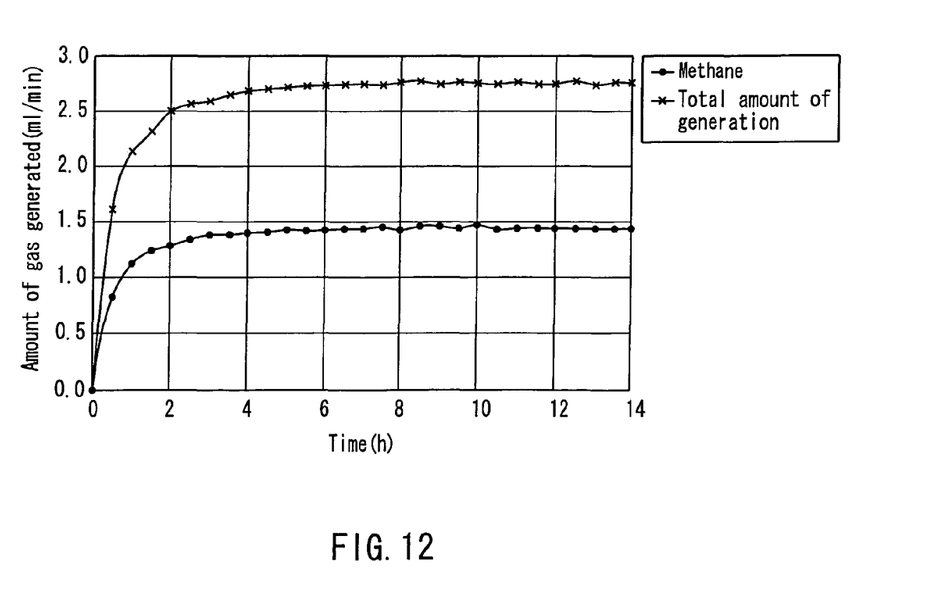
FIG. 12 is a graph showing an example of a time course of amount of methane and total gas generated in the continuous methane fermentation.

The original solution having the composition (2000 mg/l) shown in Table 1 was injected to the fermentation vessel in an amount of 200 ml per hour, and methane fermentation was carried out. Methane fermentation was carried out by using the device schematically shown in FIG. 2. The concentrations of acetic acid, short chain fatty acid, and formic acid in a discharged treated solution as well as the amounts of gas and methane generated per minute were measured every 30 minutes. The time when the gas generation was confirmed was regarded as time=0. FIG. 11 shows time course of the concentration in the discharged solution. FIG. 12 shows time course of the amount of gas generated. FIGS. 11 and 12 show that a sufficient steady state was obtained in about 8 to 10 hours from time=0. The amount of methane out of gas generated after a lapse of 6 hours was about 52% (volume ratio), and a load of the organic substance in the present example was 4.8 g/l·d as calculated based on the following formula.

$$2000 \text{ (mg/l)} \div 1000 \text{ (g/mg)} \times 200 \text{ (ml/h)} \times 24 \text{ (h}/d) \div 2000 \text{ (ml)} = 4.8 \text{ g/l} \cdot d$$

The gas generation was 2.7 ml/min when a plateau was reached, and accordingly the gas generation per hour was 2.7×60=162 ml/h. The VSS was 4000 mg/ml×2000 ml=8 g-VSS. Thus, the gas generation per VSS was 162÷8=20 ml/h·g-VSS.

The carbon digestion efficiency in the methane fermentation of the present example was obtained by performing component analysis of the original solution used for the methane fermentation and a liquid waste obtained after the methane fermentation. Further, TOC was measured with a TOC analyzer (manufactured by Shimadzu Corporation; trade name: TOC-500). The following Table 2 shows the result of the component analysis and the carbon digestion efficiency.

TABLE 2

| Composition | Concentration of original solution mg/L | TOC of original solution mg/L | Concentration of liquid waste mg/L | TOC of liquid waste mg/L | Digestion efficiency % |
|---|---|---|---|---|---|
| Acetic acid | 500 | 200 | 18 | 7 | 96.4 |
| Short chain fatty acid | 1160 | 720 | 138 | 67 | 90.7 |
| Formic acid | 340 | 89 | 35 | 9 | 89.7 |
| Total | 2000 | 1009 | 191 | 83 | 91.7 |

As shown in Table 2, the carbon digestion efficiency was 91.7%.

With respect to the short chain fatty acid, the ratio of TOC to the concentration of the original solution was 62% (720÷1160×100), and the ratio of TOC to the concentration of the liquid waste was 49% (67÷138×100). It also was shown that the fatty acid was decomposed by acid producing bacteria contained in the microorganism group used in the methane fermentation and converted into low molecular weight substances.

INDUSTRIAL APPLICABILITY

As described above, the method for producing methane gas according to the present invention provides a practical technique that enables effective utilization of organic wastes. The method for producing methane gas according to the present invention requires a short time and achieves high digestion efficiency. Therefore, organic wastes, which cost considerably to be disposed of by incineration, can be recycled into energy. Further, an apparatus for use in the production can be made compact and, for example, can be installed at geographically dispersed sites in a city as a geographically-distributed zero emission methane fermentation and power generation system.

The invention claimed is:

1. A method for producing methane gas from organic wastes, comprising:
    (a) treating organic wastes with at least one of supercritical water and sub-critical water to convert the organic wastes into low molecular weight substances;
    (b) separating the treated substances into an oil phase, a water phase, and a solid phase, so that the water phase is collected;

(c) feeding the water phase collected in step (b) into a methane fermentation vessel; and (d) subjecting the collected water phase to methane fermentation within the methane fermentation vessel, wherein in step (a), the organic wastes treated with at least one of supercritical water and sub-critical water are organic wastes that have not been subjected to methane fermentation within the methane fermentation vessel.

2. The method according to claim 1, wherein the treatment for conversion into low molecular weight substances is a treatment with sub-critical water.

3. The method according to claim 1, wherein in the treatment with sub-critical water, a treatment temperature is 440 to 553 K, and a treatment pressure is 0.8 to 6.4 MPa.

4. The method according to claim 1, wherein a time taken for the treatment for conversion into low molecular weight substances is 1 to 20 minutes.

5. The method according to claim 1, wherein the treatment for conversion into low molecular weight substances is performed continuously.

6. The method according to claim 1, wherein the water phase contains organic acid.

7. The method according to claim 6, wherein the organic acid includes acetic acid.

8. The method according to claim 1, wherein a time for the methane fermentation is in a range of 5 to 48 hours.

9. The method according to claim 1, wherein carbon digestion efficiency in the methane fermentation is 90% or more.

10. The method according to claim 1, wherein the organic waste is activated sludge.

11. The method according to claim 1, further comprising separating and collecting a useful material generated in the treatment for conversion into low molecular weight substances.

12. The method according to claim 11, wherein the useful material generates at least one of phosphoric acid, organic acid, fatty acid, amino acid, and sugar.

13. The method according to claim 11, wherein by adjusting at least one of a treatment temperature and a treatment time in the treatment for conversion into low molecular weight substances, the useful material is allowed to be generated selectively.

* * * * *